United States Patent [19]

Daubenspeck

[11] Patent Number: 4,787,627

[45] Date of Patent: Nov. 29, 1988

[54] VISUAL PRESSURE MONITOR FOR RESPIRATORY BREATHING APPARATUS

[75] Inventor: J. Andrew Daubenspeck, West Lebanon, N.H.

[73] Assignee: The Trustees of Dartmouth College, Hanover, N.H.

[21] Appl. No.: 48,655

[22] Filed: May 12, 1987

[51] Int. Cl.$^4$ ............................................. A63B 23/00
[52] U.S. Cl. ..................................... 272/99; 73/715; 73/730; 128/716
[58] Field of Search ........................ 128/716; 272/99; 73/715, 730

[56] References Cited

U.S. PATENT DOCUMENTS

| | | | |
|---|---|---|---|
| 1,781,735 | 11/1930 | Scott. | |
| 2,503,372 | 4/1950 | Bagley | 73/715 X |
| 3,826,247 | 7/1974 | Ruskin et al. | 128/2.08 |
| 3,958,565 | 5/1976 | Wright | 128/2.08 |
| 4,041,935 | 8/1977 | Garbe | 272/99 X |
| 4,171,804 | 10/1979 | Thead, Jr. | 272/99 |
| 4,233,990 | 11/1980 | Yardley | 272/99 X |
| 4,284,083 | 8/1981 | Lester | 128/725 |
| 4,441,506 | 4/1984 | McCombs et al. | 128/728 |
| 4,499,905 | 2/1985 | Greenberg et al. | 272/99 X |
| 4,638,812 | 1/1987 | Häkkinen | 128/726 |

Primary Examiner—Lloyd L. King
Attorney, Agent, or Firm—Hamilton, Brook, Smith & Reynolds

[57] ABSTRACT

An apparatus to visually and instantaneously indicate the pressure at the mouthpiece of a respiratory apparatus. The apparatus comprises a rigid tube with an aperture formed in the tube wall. Over the tube and covering the aperture is a flexible membrane which will deflect when the internal pressure differs from the external pressure. Mounted in communication with the flexible membrane is a pointer mechanism which provides a visual indication of the magnitude of the deflection of the flexible membrane.

4 Claims, 1 Drawing Sheet

VISUAL PRESSURE MONITOR FOR RESPIRATORY BREATHING APPARATUS

BACKGROUND OF THE INVENTION

Persons suffering from chronic obstructive pulmonary disease (COPD) and others with various respiratory disorders often experience a decreased ability to inhale. For example, while a healthy person may develop a maximum inhalation pressure of approximately 80–100 cm $H_2O$, a person with a respiratory disorder may be able to develop a maximum inhalation pressure of only half that. As a means of rebuilding respiratory strength, physicians often prescribe a protocol of respiratory therapy involving inhalation resistance training.

In current respiratory therapy practice, it is useful to prescribe respiratory muscle training programs using simple flow resistance apparatus for specified training protocols over extended periods of time in the patients' homes. There has been no way to provide these patients with an indication of how much force to exert with their inspiratory muscles in order to insure an effect of the exercise. Furthermore, it is suspected that patients adapt their breathing pattern to minimize the effort of breathing and, thus, the effect of the prescribed protocol.

By providing patients with some type of indication of their performance during inspiratory exercise, it is believed that the exercise would prove to be more effective as it would tend to prevent conscious or subconscious cheating during the exercise. Measurement of patients' performance, however, is difficult due to the small pressures (5–20 cm $H_2O$) involved.

SUMMARY OF THE INVENTION

This invention pertains to a visual pressure monitor for respiratory breathing apparatus. More particularly the invention pertains to a simple and inexpensive device useful for providing an indication of the performance of a patient during respiratory exercise. In its most basic form, the invention is a visual pressure monitor for respiratory breathing apparatus comprising:

(a) a rigid breathing tube containing an aperture in the wall thereof;
(b) a flexible membrane covering said aperture;
(c) a pointer mechanism in communication with the flexible membrane which is moveable to indicate deflection in the flexible membrane; and,
(d) a means for providing a visual indication of the magnitude of deflection of the flexible membrane.

As patients inhale through the rigid breathing tube, the pressure within the rigid breathing tube drops. This pressure drop causes the flexible membrane to deflect in an inward, or concave manner. As the pointer mechanism is in communication with the flexible membrane, it moves in an amount relative to the deflection of the membrane. A scale is located behind the pointer mechanism to give a visual indication of the magnitude of membrane deflection and the associated pressure change in the rigid breathing tube.

The above and other features of the invention including various novel details of construction and combinations of parts will now be more particularly described with reference to the accompanying drawings and pointed out in the claims. It will be understood that the particular apparatus embodying the invention is shown by way of illustration only and not as a limitation of the invention. The principles and features of this invention may be employed in varied and numerous embodiments without departing from the scope of the invention.

DETAILED DESCRIPTION OF THE INVENTION

This invention is a device for measuring inspiratory pressures of subjects participating in respiratory exercise. The device comprises a plastic tube of appropriate size to match the aperture of a respiratory exercise apparatus, and has an aperture bored in one position on the tube wall. The aperture is covered by a flexible membrane which deflects inwardly when the pressure in the tube drops below atmospheric pressure such as when a subject inhales through the tube. By measuring deflection of the flexible membrane, it is possible to indicate to the subject the relative force of the inhalation.

Figure 1:
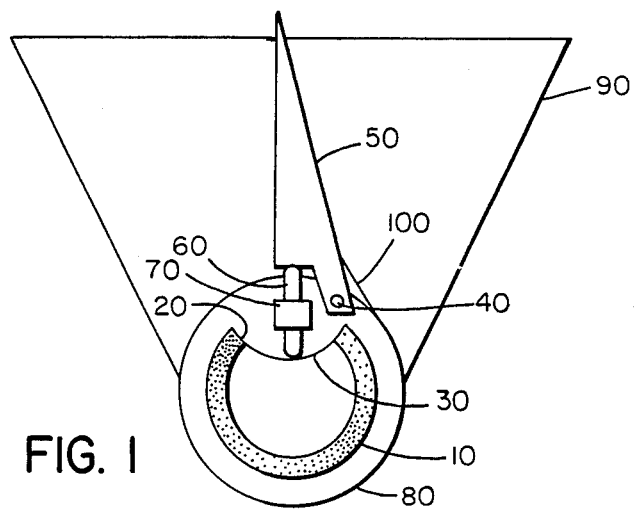
FIG. 1 is a schematic representation of one embodiment of a visual pressure monitor for respiratory breathing apparatus.

FIG. 1 illustrates one embodiment of the invention. In FIG. 1, a rigid breathing tube 10, preferably made of plastic, has an aperture 20, bored into the tube wall. Covering the aperture is a flexible membrane 30, which in the preferred embodiment, consists of a thin tube of latex rubber which has been fitted over the breathing tube 10 in such a manner that it entirely covers the aperture 20. Mounted to the outside of a mounting bracket 80, at the edge of the membrane-covered aperture is a pivot 40 and indicating pointer or needle 50 which is in communication with the flexible membrane 30. In the preferred embodiment, a pushrod 60, mounted in a rod guide 70, is attached to the mounting bracket 80. The pushrod 60 is in contact with both the flexible membrane 30 and the pointer 50. As the membrane 30 moves, the pushrod 60 acting as a lateral support for the pointer 50 also moves in the same direction. This causes the pointer 50 to deflect, and the magnitude of this deflection may be read off a scale 90, located behind the pointer 50 to give an instantaneous indication of the relative pressure in the breathing tube, thereby providing the subject with an indication of the force of the inhalation. Like the rod guide 70, the scale 90, is also attached to the mounting bracket 80. A spring 100 is provided to maintain a force on the pointer 50, causing it to maintain contact with the pushrod 60.

Figure 2:
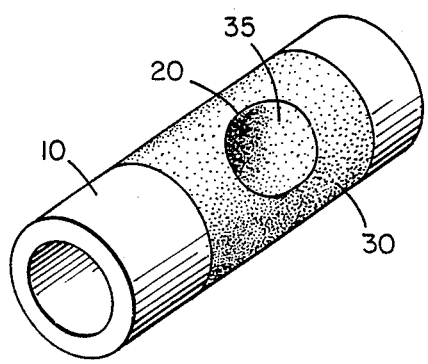
FIG. 2 is a schematic representation of a tube and flexible membrane assembly of the invention.

FIG. 2 depicts the tube/membrane subassembly of the invention. The rigid breathing tube 10, contains an aperture 20, which has been formed in the tube wall. Around the tube 10, and entirely covering the aperture 20, is a flexible membrane sleeve 30, preferably of a material such as latex rubber. The covering of the flexible membrane 30 over the aperture 20, creates a distendable surface 35. It is the relative position of this distendable surface 35, which is measured to determine the relative force of the subject's inhalation.

Figure 3:
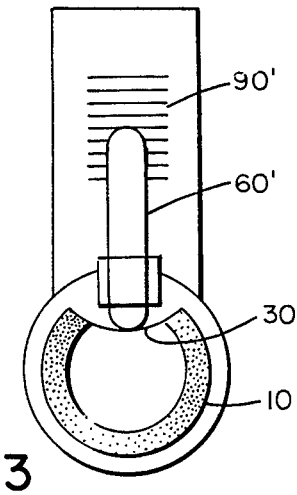
FIG. 3 is a schematic representation of a second embodiment of the invention.

FIG. 3 depicts a second embodiment of the invention. In FIG. 3, the pivot, the scale with horizontal markings, the pointer, and the spring have been removed. In their place is a longer pushrod 60' and a scale with vertical markings 90'. As the flexible membrane 30 deflects upward and downward due to the pressures in the rigid breathing tube 10, the pushrod 60' will also deflect vertically. These deflections may be read directly on the vertical scale 90' thereby providing the subject with an instantaneous indication of the relative pressure in the breathing tube and thus, the force of inhalation.

EQUIVALENTS

Those skilled in the art will recognize, or be able to ascertain, using no more than routine, experimentation, many equivalents to the specific embodiments of the invention described herein. For example, rather than having the flexible membrane be a sleeve which entirely surrounds the rigid breathing tube, the membrane may be a small circle of material which is firmly glued around the perimeter of the aperture. Such equivalents are intended to be encompassed by the following claims.

I claim:

1. A visual pressure monitor for respiratory breathing apparatus comprising:
   (a) a rigid breathing tube containing an aperture in the wall thereof;
   (b) a flexible membrane covering said aperture;
   (c) a pointer mechanism in communication with the flexible membrane which is movable to indicate deflection in the flexible membrane;
   (d) a pushrod located between the flexible membrane and the pointer mechanism; and
   (e) a means for providing a visual indication of the magnitude of deflection of the flexible membrane.

2. An apparatus as in claimed in claim 1 wherein the pointer mechanism is a vertically deflectable pushrod which is in direct communication with the flexible membrane.

3. An apparatus as claimed in claim 1 wherein the rigid breathing tube is in communication with a respiratory exercisor.

4. An apparatus as claimed in claim 1 wherein inhalation through the rigid breathing tube causes a pressure drop within the rigid breathing tube; said pressure drop causing a deflection of the flexible membrane which is indicated by the pointer mechanism to provide a subject with an instantaneous measurement of the relative force of the inhalation.

* * * * *